(12) United States Patent
Kobayashi et al.

(10) Patent No.: US 12,414,756 B2
(45) Date of Patent: Sep. 16, 2025

(54) ULTRASONIC PROBE AND ULTRASONIC DIAGNOSTIC APPARATUS

(71) Applicant: CANON MEDICAL SYSTEMS CORPORATION, Otawara (JP)

(72) Inventors: Yusuke Kobayashi, Nasushiobara (JP); Hiroyuki Shikata, Nasushiobara (JP); Makoto Ogi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 44 days.

(21) Appl. No.: 18/353,386

(22) Filed: Jul. 17, 2023

(65) Prior Publication Data

US 2024/0023934 A1 Jan. 25, 2024

(30) Foreign Application Priority Data

Jul. 21, 2022 (JP) ................................. 2022-116718

(51) Int. Cl.
*A61B 8/00* (2006.01)
(52) U.S. Cl.
CPC ............ *A61B 8/4461* (2013.01); *A61B 8/429* (2013.01); *A61B 8/4494* (2013.01); *A61B 8/4477* (2013.01)
(58) Field of Classification Search
CPC ..... A61B 8/4461; A61B 8/429; A61B 8/4494; A61B 8/4477; A61B 8/085; A61B 8/4281; A61B 8/4444; A61B 8/4455
See application file for complete search history.

(56) References Cited

U.S. PATENT DOCUMENTS

| 2002/0068871 A1* | 6/2002 | Mendlein | A61B 8/4209 600/459 |
| 2003/0011285 A1* | 1/2003 | Ossmann | G01S 15/8927 310/334 |
| 2005/0070801 A1* | 3/2005 | Yamashita | A61B 8/4281 600/459 |
| 2007/0161903 A1* | 7/2007 | Yamashita | A61B 8/14 600/459 |
| 2007/0197914 A1* | 8/2007 | Kosaku | A61B 8/0841 600/459 |
| 2013/0072802 A1* | 3/2013 | Hozumi | A61B 8/4281 600/472 |
| 2017/0000459 A1* | 1/2017 | Shikata | A61B 8/4281 |
| 2017/0135673 A1* | 5/2017 | Bruestle | G01S 7/52079 |
| 2017/0164926 A1* | 6/2017 | Spicci | A61N 7/00 |

FOREIGN PATENT DOCUMENTS

JP 2017-12381 A 1/2017

* cited by examiner

*Primary Examiner* — Adil Partap S Virk
(74) *Attorney, Agent, or Firm* — Oblon, McClelland, Maier &Neustadt, L.L.P.

(57) ABSTRACT

According to one embodiment, the ultrasonic probe includes a transducer group, an acoustic transmission layer, and a protective material. The transducer group has a plurality of transducers transmitting ultrasonic waves. The acoustic transmission layer transmits the ultrasonic waves transmitted by the transducer group. The protective material protects the transducer group and the acoustic transmission layer. A width of the transducer group in an elevation direction and an opening width of the protective material at the position corresponding to the body contact surface of the acoustic transmission layer are almost identical. The transducer group is provided at a predetermined distance from the body contact surface of the acoustic transmission layer.

11 Claims, 9 Drawing Sheets

CONV. EX(1):CONTACT PORTION:SILICONE

CONV. EX(2): CONTACT PORTION:POLYMETHYLPENTENE

ULTRASONIC PROBE AND ULTRASONIC DIAGNOSTIC APPARATUS

CROSS-REFERENCE TO RELATED APPLICATIONS

This application claims the benefit of priority of Japanese Patent Application No. 2022-116718, filed Jul. 21, 2022, the entire contents of which are incorporated herein by reference.

FIELD

Embodiments described herein relate generally to an ultrasonic probe and an ultrasonic diagnostic apparatus.

BACKGROUND

Generally, ultrasonic probes connected to ultrasonic diagnostic apparatuses include one-dimensional array probes (hereinafter referred to as 1D probe) in which multiple transducers are arrayed in one direction (azimuth direction), two-dimensional array probes (hereinafter referred to as 2D probe) in which multiple transducers are arrayed in two directions (azimuth direction and elevation direction) and the ultrasonic beam can be swept electronically in those two directions, a multi-row array probe (hereinafter referred to as 1.5D probe) in which multiple transducers are arrayed in those two directions but the ultrasound beam cannot be swept in the elevation direction.

Among array-type ultrasonic probes, 1D and 1.5D probes include an acoustic lens to converge the ultrasonic beam along the scanning plane to obtain a thin tomogram. The acoustic lens is required to be made of a material whose sound velocity is different from that of the body surface and the organism (soft tissue) and whose acoustic impedance is close to that of the body surface and the organism. Silicone rubber, which has a lower sound velocity than the organism, and polymethylpentene, which has a higher sound velocity than the organism, are known as materials that satisfy these requirements.

When acoustic lens is made of silicone rubber, the acoustic lens and the side cover made of plastic are generally bonded with silicone adhesive to maintain waterproofness. However, since the silicone adhesive itself has low rigidity and low adhesive strength to the plastic material, a certain adhesive area is required to maintain reliability of adhesion. Accordingly, the width (thickness) of the body contact surface of the ultrasonic probe is increased by the amount of adhesion area.

When acoustic lens is made of polymethylpentene, the width of the body contact surface can be reduced because the cover is no longer necessary, but the body contact surface does not have the elasticity of silicone rubber.

When conventional ultrasonic probes are used for ultrasonic imaging of the inside of the body (chest organs such as the heart and liver) from the body surface, it is essential to scan from between the ribs because the chest organs are located in the area covered by the ribs. Especially during ultrasonic imaging of the liver, when scanning in a situation where it is unclear whether or not an abnormal site exists, blind spots in the area behind the ribs may lead to the overlooking of abnormalities. The operator places the ultrasonic probe on the body surface between the ribs and tilts the ultrasonic probe to scan behind the ribs using the conventional ultrasonic probe.

However, when the width of the body contact surface of the ultrasonic probe is large, the operator may tilt the ultrasonic probe to a larger angle, resulting in the imaging area being out of the intercostal space. When the ultrasonic probe is tilted largely, a blind spot is created behind the ribs, making it impossible to use the intercostal space as the imaging area. Further, if the operator tries to perform ultrasonic imaging by pressing the ultrasonic probe deeply into the patient to narrow the blind spot, the burden on the patient who is pressed by the ultrasonic probe increases.

When silicone rubber, a flexible material, is used as the acoustic lens material, if the ultrasonic probe is accidentally dropped on the floor or bumped against other devices, the impact received by the acoustic lens will be transmitted to the transducer, causing the transducer to fail.

DETAILED DESCRIPTION

Hereinbelow, a description will be given of an ultrasonic probe and an ultrasonic diagnostic apparatus according to embodiments of the present invention with reference to the drawings.

In general, according to one embodiment, the ultrasonic probe includes a transducer group, an acoustic transmission layer, and a protective material. The transducer group has a plurality of transducers transmitting ultrasonic waves. The acoustic transmission layer transmits the ultrasonic waves transmitted by the transducer group. The protective material protects the transducer group and the acoustic transmission layer. A width of the transducer group in an elevation direction and an opening width of the protective material at the position corresponding to the body contact surface of the acoustic transmission layer are almost identical. The transducer group is provided at a predetermined distance from the body contact surface of the acoustic transmission layer.

Figure 1:
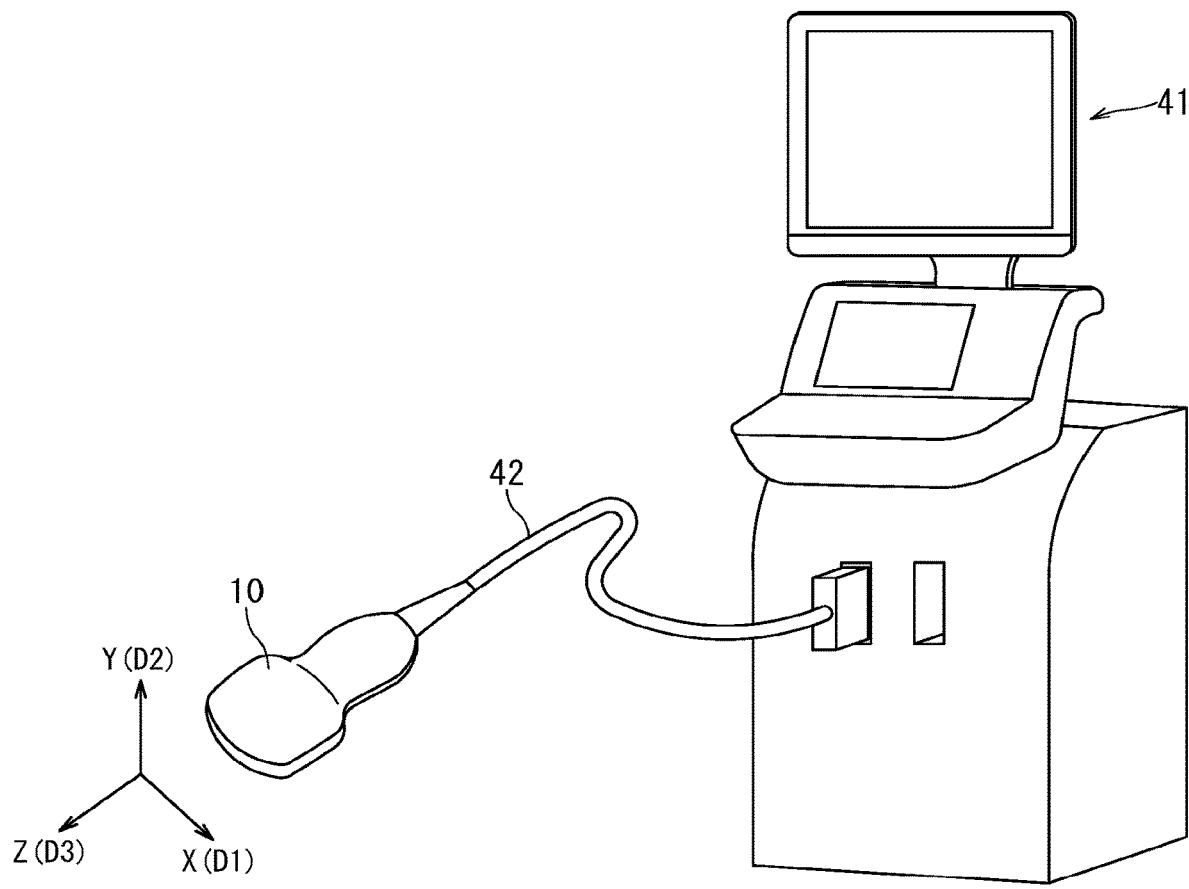
FIG. 1 is a schematic diagram illustrating a configuration of an ultrasonic probe and an ultrasonic diagnostic apparatus to which the ultrasonic probe is detachably connected.

FIG. 1 is a schematic diagram illustrating a configuration of an ultrasonic probe 10 and an ultrasonic diagnostic apparatus 41 to which the ultrasonic probe 10 is detachably connected.

The ultrasonic probe 10 is used for imaging the morphology of organs and other parts inside the body by approaching from the body surface. Hereafter, ultrasonic probe is simply referred to as a probe.

The probe 10 transmits and receives ultrasonic waves to and from the living body (object) according to the control by the ultrasonic diagnostic apparatus 41. The probe 10 according to this embodiment is an abdominal convex-type 1D probe. The abdominal convex-type 1D probe is used for ultrasonic imaging of the internal organs of the chest, such as the heart and liver, and is particularly effective when scanning of the entire liver is required. The probe 10 has a plurality of transducers, and the plurality of transducers are arranged one-dimensionally along the first direction D1 (azimuth direction) to form a transducer group. The probe 10 in which each transducer is arranged one-dimensionally is called a 1D probe. Such 1D probe performs electron scanning along the first direction D1, so the first direction D1 is sometimes called the scan direction.

The thickness direction of the probe 10 orthogonal to the first direction D1 is called the second direction D2 (elevation direction). In 1D probes, the beam formation in the second direction D2 is often performed by the ultrasound lens. Therefore, the second direction D2 is sometimes called the lens direction.

The direction orthogonal to each of the first direction D1 (azimuth direction) and the second direction D2 (elevation direction) is called the third direction (D3). The first direction D1, the second direction D2, and the third direction are orthogonal to each other, as shown in FIG. 1, and may correspond, for example, to the Cartesian coordinate system in the X, Y, and Z directions.

The probe 10 is connected to the ultrasonic diagnostic apparatus 41 via a cable 42. The probe 10 includes a sector scanning type, a linear scanning type, and a convex scanning type, which are selected according to the diagnostic site. The specific structure of probe 10 will be described below.

The ultrasonic diagnostic apparatus 41 controls the operation of the probe 10 to transmit drive pulses to the probe 10 to drive the piezoelectric elements of the probe 10. The ultrasonic diagnostic apparatus 41 also controls the operation of the probe 10 to receive electrical reception signals converted by the piezoelectric elements of the probe to generate ultrasound images such as B-mode images.

Before describing the probe 10, a conventional probe is described as a comparative example to the probe 10.

Figure 2A:
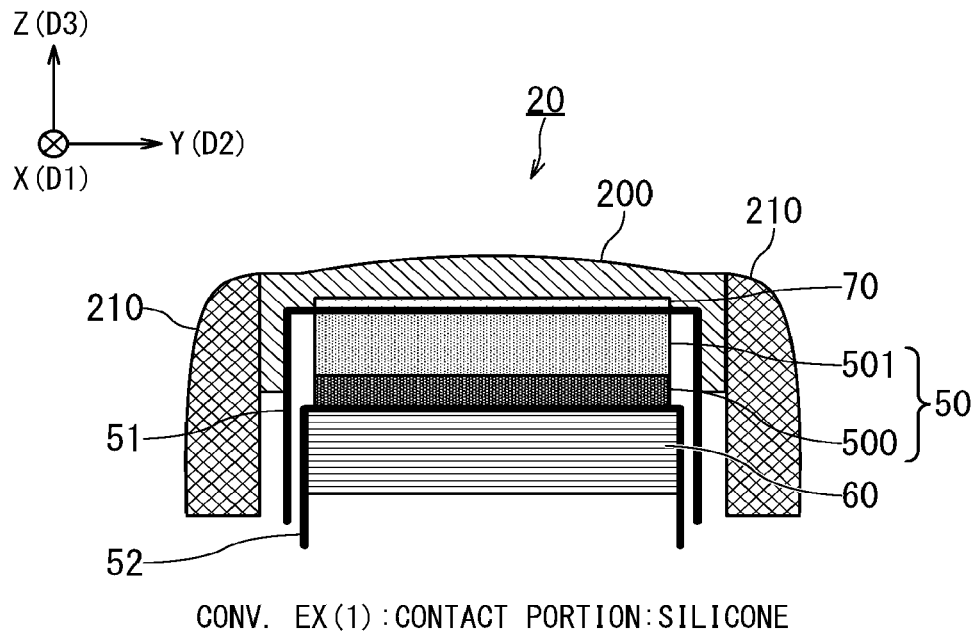
FIG. 2A is a cross sectional view in the second direction D2 showing the structure of the tip of the probe according to the conventional example (1).
Figure 2B:
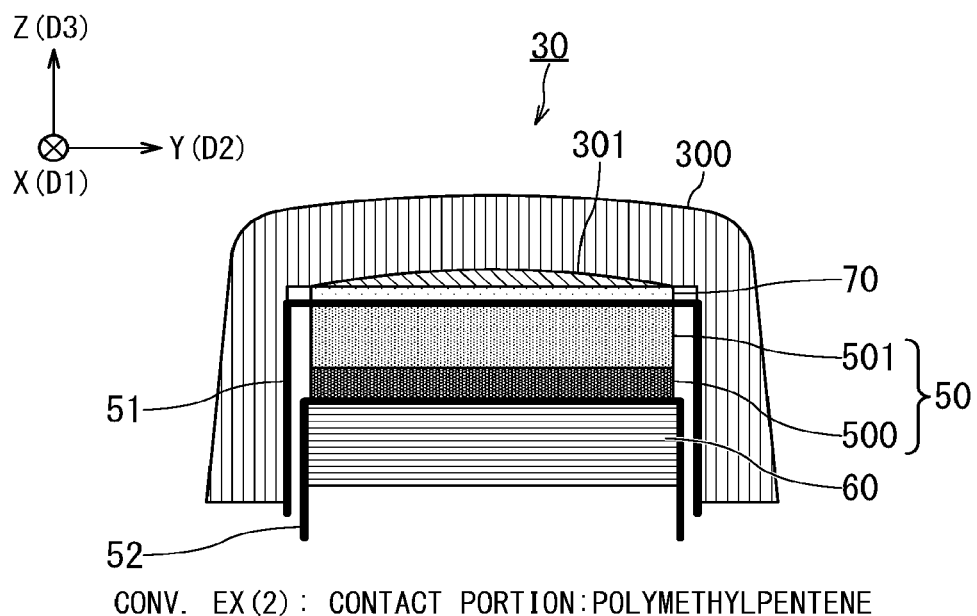
FIG. 2B is a cross sectional view in the second direction D2 showing the structure of the tip of the probe according to the conventional example (2).

FIG. 2A is a cross sectional view in the second direction D2 showing the structure of the tip of the probe according to the conventional example (1). FIG. 2B is a cross sectional view in the second direction D2 showing the structure of the tip of the probe according to the conventional example (2). Both FIGS. 2A and 2B are cross-sectional views showing a part where the width in the first direction D1 are approximately bisected.

Conventional example (1) and conventional example (2) have, as a common configuration, a transducer group 50, a backing material 60, a second acoustic matching layer 70, a GND (ground) layer 51, and an FPC (Flexible Printed Circuits) 52 as a signal layer.

The transducer group 50 includes a plurality of piezoelectric elements 500 arranged in the first direction D1 (paper depth direction) and an acoustic matching layer 501. The piezoelectric elements 500 are electroacoustic conversion elements that have the function of converting electric signals into ultrasonic waves (transmitted ultrasonic waves) during transmission and converting reflected ultrasonic waves (received ultrasonic waves) into electric signals (received signals) during reception.

The acoustic matching layer 501 is provided to stepwisely reduce the difference in acoustic impedance between the piezoelectric element 500 and the living body.

The backing material 60 is provided on the back side of the transducer group 50 (i.e., opposite the body contact surface of the probe 10). The backing material 60 is provided to suppress the resonance of the piezoelectric element 500, thereby generating short pulse waves, and also to absorb and attenuate unwanted ultrasonic signals generated on the back side of the piezoelectric element 500. The second acoustic matching layer 70 is provided in the front direction of the transducer group 50 for, like the acoustic matching layer 501, reducing the acoustic impedance difference between the piezoelectric element 500 and the living body.

The FPC 52 and the GND layer 51 are ground layers, each consisting of a flexible printed substrate, which supplies electrical signals to individual piezoelectric elements 500 and a plurality of ground wires.

In the conventional example (1) shown in FIG. 2A, the contact portion 200 with the living body is an acoustic lens and is made of silicone rubber. Pure silicone rubber has a sound velocity of about 1000 m/sec and an acoustic impedance of about 1 MRayl, which is lower than the 1.5 MRayl acoustic impedance of the medium, so the specific gravity is generally adjusted by using a material with high specific gravity as a filler material, for example, fine powder made of silica. Silicone rubber is most commonly used because silicone rubber has a slower sound velocity than the living body, and the convex lens provides a convergence effect, which is favorable in contact with the living body.

On the other hand, silicone rubber is a flexible material that easily transmits shock to the transducer group 50. Therefore, a rigid side member 210 is provided to cover the side of the tip of the probe 20 so as to prevent the probe 20 from failure due to a drop impact and the like, and to secure the probe 20 to the gripping portion of the probe 20. Generally, the side member 210 is formed of a plastic material.

The contact portion 200 (acoustic lens 200) and the side member 210 are generally bonded with silicone adhesive which is waterproof, but a certain adhesive area is required to maintain reliability because the silicone adhesive itself has low rigidity and low adhesive strength to the plastic material. Therefore, as shown in FIG. 2A, the acoustic lens 200 is extended to the side of the transducer group 50, and is bonded to the side member 210 at the side of the acoustic lens 200.

In this method, the width of the tip of the probe 20 in the second direction D2 is increased by the extended portion of the acoustic lens 200. Therefore, the body contact width in the second direction D2 (i.e., foot print width FPW) is larger than the acoustic effective aperture in the second direction D2 (width of the transducer group 50 in the second direction D2).

In this specification, an example is given where the foot print width FPW is defined as the width in the second direction D2 at a position 2 mm away from the top of the body contact surface in the lens direction D2.

In the probe 30 according to the conventional example (2) shown in FIG. 2B, the contact portion 300 that contacts with the living body is formed of polymethylpentene. When polymethylpentene is used for the contact portion 300, the foot print width FPW can be reduced because polymethylpentene is a plastic material and the contact portion 300 can serve as a side member for impact resistance. A convex filling layer 301, whose sound velocity is slower than that of the body tissue, can also be provided between the contact portion 300 and the transducer group 50 to provide a focus effect.

However, since polymethylpentene is a plastic material, the probe 30 according to the conventional example (2) has a hard body contact surface and generally tends to repel the jelly material applied as the acoustic medium between the living body and the probe 30.

Figure 3:
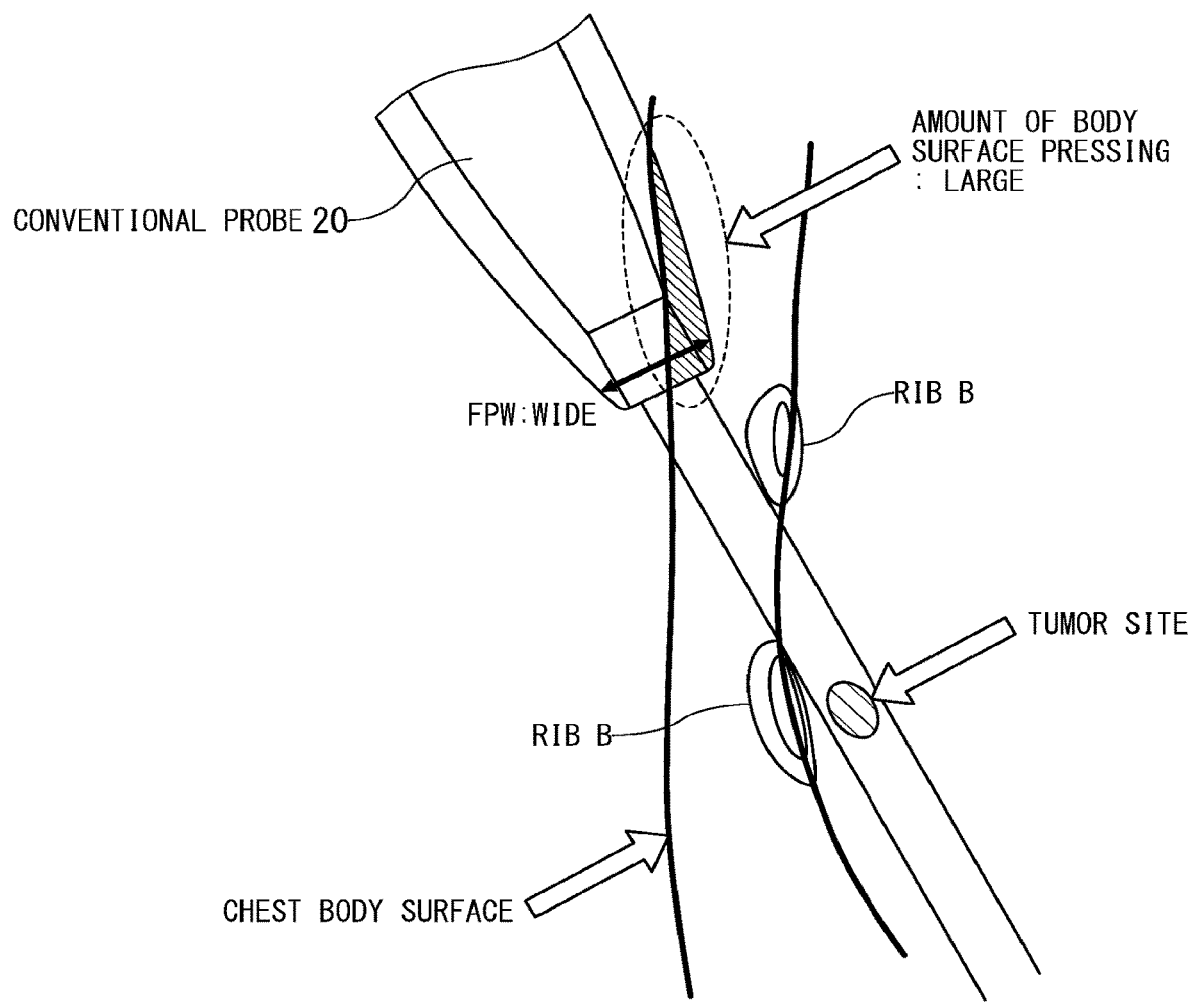
FIG. 3 illustrates problems related to the foot print width FPW of the probe according to the conventional example (1).

FIG. 3 illustrates problems related to the foot print width FPW of the probe 20 according to the conventional example (1).

When the probe 20 according to the conventional example (1) is used, the width FPW of the body contact surface of probe 20 becomes large, which causes problems in ultrasonic imaging using such probe 20. For example, when ultrasonic imaging is performed from the body surface to image the inside of the body (chest organs such as the heart and liver), scanning from between the ribs is necessary because the chest organs are located in the area covered by the ribs. When the operator tilts the probe 20 widely/largely for ultrasonic imaging behind the ribs, if the width FPW of the body contact surface of probe 20 is large, part of the imaging area of probe 20 is likely to be out of the intercostal space and easily obstructed by the ribs. Particularly in the case of ultrasonic imaging of the liver, when it is not known whether an abnormal site exists or not, if a part of the imaging area of the probe 20 overlaps with the ribs, abnormalities behind the ribs may be overlooked. This may also lead to pressing the probe 20 deeply against the body surface, which increases the burden on the patient being pressed against the probe 20.

As shown in FIG. 3, to perform ultrasonic imaging of a living body using the probe 20, the operator places the probe 20 on the body surface and tilts the probe 20 to image the living body from between the ribs B (intercostal space). Since the width FPW of the body contact surface of the probe 20 (illustrated in FIGS. 2 and 3) is large, when the operator tilts the probe 20 significantly to image the area behind the ribs, part of the imaging area of the probe 20 can easily deviate from the intercostal space and fall on the ribs B, causing blind spots to occur. In addition, when the operator presses the probe 20 deeply against the body surface to narrow the contact portion (the shaded area shown in FIG. 3), it increases the burden on the patient who is pressed by the probe 20.

When the body contact width (foot print width FPW) is reduced to eliminate such inconvenience while maintaining the configuration of the probe 20 of the conventional example (1), the width of the transducer group 50 in the second direction D2, that is, the acoustically effective aperture, becomes smaller. When the acoustic effective aperture becomes smaller, the image quality of sites far from the probe 20 (deep areas) will deteriorate and the signal-to-noise ratio (S/N ratio) will decrease.

To solve these inconveniences, the probe 10 according to the present embodiment shown in FIG. 1 provides a configuration and structure that enables a reduction in the body contact width (foot print width FPW) without reducing the acoustic effective aperture.

Figure 4:
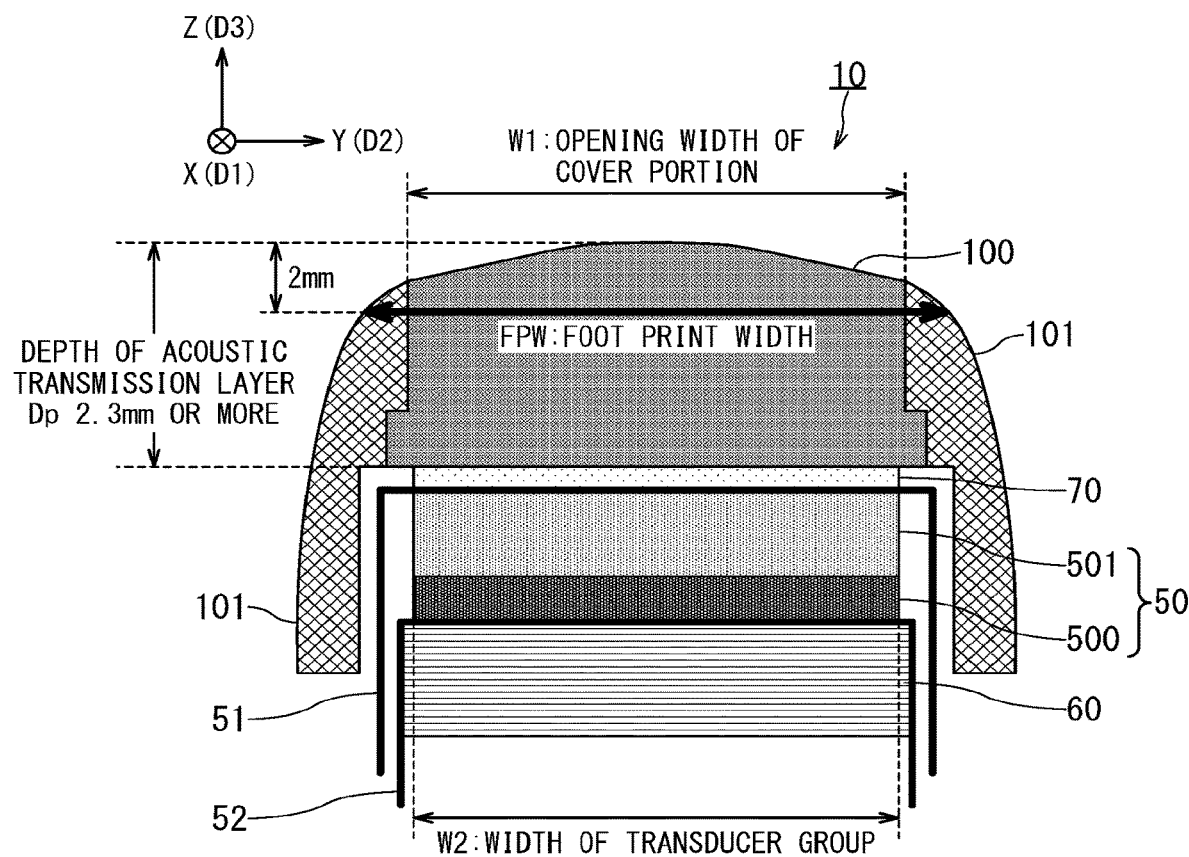
FIG. 4 illustrates an example of the configuration of the probe shown in FIG. 1.

FIG. 4 illustrates an example of the configuration of the probe 10 shown in FIG. 1. FIG. 4 is a cross sectional view in the second direction D2 showing the structure of the tip portion of the probe 10, same as FIGS. 2A and 2B, and a cross sectional view of a cross section approximately bisecting the width in the first direction D1.

The probe 10 has a transducer group 50 consisting of a plurality of transducers 500 (piezoelectric elements 500) arranged along the first direction D1 and transmitting and receiving ultrasonic waves, a backing material 60, a GND (ground) layer 51, and an FPC (Flexible Printed Circuits (FPC) 52 as the signal layer 52. These configurations are substantially the same as those in conventional examples (1) and (2) shown in FIGS. 2A and 2B, therefore the explanation is omitted.

The probe 10 has a convex surface in the third direction D3 orthogonal to the first direction D1, and the probe 10 has at least an acoustic transmission layer 100 that transmits the sound generated by the transducer group 50 and a protective material that protects the transducer group 50 and the acoustic transmission layer 100. The protective material includes a cover 101 that covers at least part of the lateral side of the transducer group 50. The cover 101 is formed, for example, using a plastic material.

The acoustic transmission layer 100 and the cover 101 can each be made as a molded product, and the acoustic transmission layer 100 and the cover 101 can be bonded using an adhesive. The acoustic transmission layer 100 can also be cast molded, and in this case, the probe 10 can be fabricated without using any adhesive.

The probe 10 reduces the foot print width FPW by making the distance (predetermined distance) between the acoustic emitting side of the transducer group 50 and the body contact surface, i.e., the depth Dp of the acoustic transmission layer 100, larger than the distance between the acoustic emitting side of the transducer group 50 in the conventional example (1) and the body contact surface.

Specifically, the depth Dp of the acoustic transmission layer 100 is made to be 2.3 mm or more. The larger depth Dp of the acoustic transmission layer 100 allows a sufficient bonding area to be secured even when the side surface of the acoustic transmission layer 100 and the cover 101 are bonded directly, whereby the acoustic transmission layer 100 and cover 101 can be fixed with sufficient strength.

Accordingly, it is no longer necessary to provide an extended portion of the acoustic lens 200 extending to the side of the transducer group 50 as in the probe 20 according to the conventional example (1), and the foot print width FPW can be reduced.

The increased depth Dp of the acoustic transmission layer 100 may increase the propagation loss of the ultrasonic signal. However, in this embodiment, by forming the acoustic transmission layer 100 using a material with low attenuation of ultrasonic signals and a sound velocity close to that of the living body, the increase in propagation loss of ultrasonic signals and the focusing effect caused by different sound velocity from the living body are suppressed.

Specifically, a material having the following properties is used as the material of the acoustic transmission layer 100.
(a) having a sound velocity between 1500 m/sec and less than 1600, inclusive
(b) having an acoustic impedance between 1.4 MRayl and 1.6 MRayl, inclusive
(c) having an attenuation of about 0.03*0.10 dB/mmMHz An example of a material that satisfies the above conditions is a butadiene rubber-based material. In the probe 10, the acoustic transmission layer 100 is formed with a butadiene rubber-based material.

Butadiene rubber is more flexible than polymethylpentene and has a higher affinity for jelly material as the acoustic medium. Therefore, the problems of the probe 30 according to the conventional example (2), that a) the body contact surface is hard and b) the jelly material as the acoustic medium is easily repelled, can be solved by the probe 10 having the acoustic transmission layer 100 formed by butadiene rubber.

Furthermore, in the probe 10, the protective material is provided such that a width of the transducer group 50 in the elevation direction and an opening width of the protective material at the position corresponding to the body contact surface of the acoustic transmission layer 100 are almost identical, e.g., the difference between each other is 1.0 mm or less. The difference between the cover opening width W1 and the width W2 of the transducer group 50 is, for example, between 0 mm and 1 mm. This configuration suppresses the acoustic propagation loss caused by the acoustic shielding of the cover 101.

By having the same or a smaller difference between the cover opening width W1 and the width W2 of the transducer group 50, i.e., the acoustically effective aperture, deterioration in image quality and signal-to-noise ratio (S/N ratio) degradation at sites distant from the probe 10 (deep areas) can be prevented.

Figure 5A:
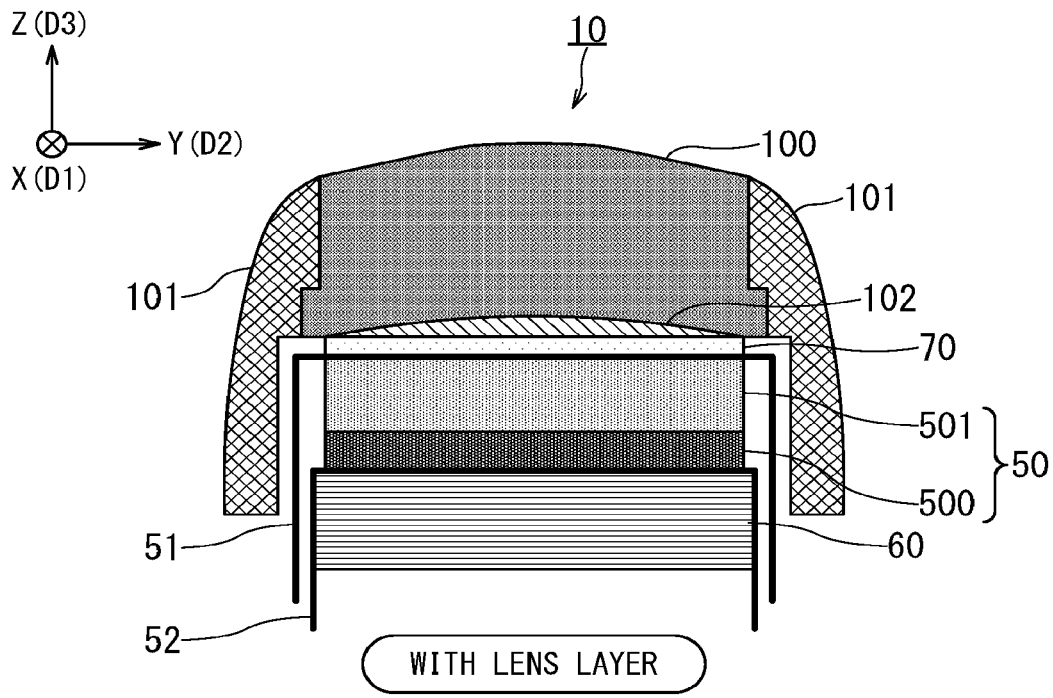
FIG. 5A illustrates the first variation of the probe shown in FIG. 1.

FIG. 5 shows variants of the probe 10 shown in FIG. 1. The first variation shown in FIG. 5A has an acoustic lens layer 102 between the acoustic transmission layer 100 and the transducer group 50. By making the sound velocity of the acoustic lens layer 102 different from that of the body tissue, the probe 10 is provided with an acoustic focus function.

When the sound speed of the acoustic lens layer 102 is slower than that of the body tissue, the cross section of the acoustic lens layer 102 in the second direction D2 should show a convex surface. Conversely, when the sound speed of the acoustic lens layer 102 is faster than that of the acoustic transmission layer 100, the cross section of the acoustic lens layer 102 in the second direction D2 should show a concave surface. The thickness of the acoustic lens layer 102 (thickness of the thickest portion) may be, for example, 0.3 mm or more and 0.9 mm or less.

Figure 5B:
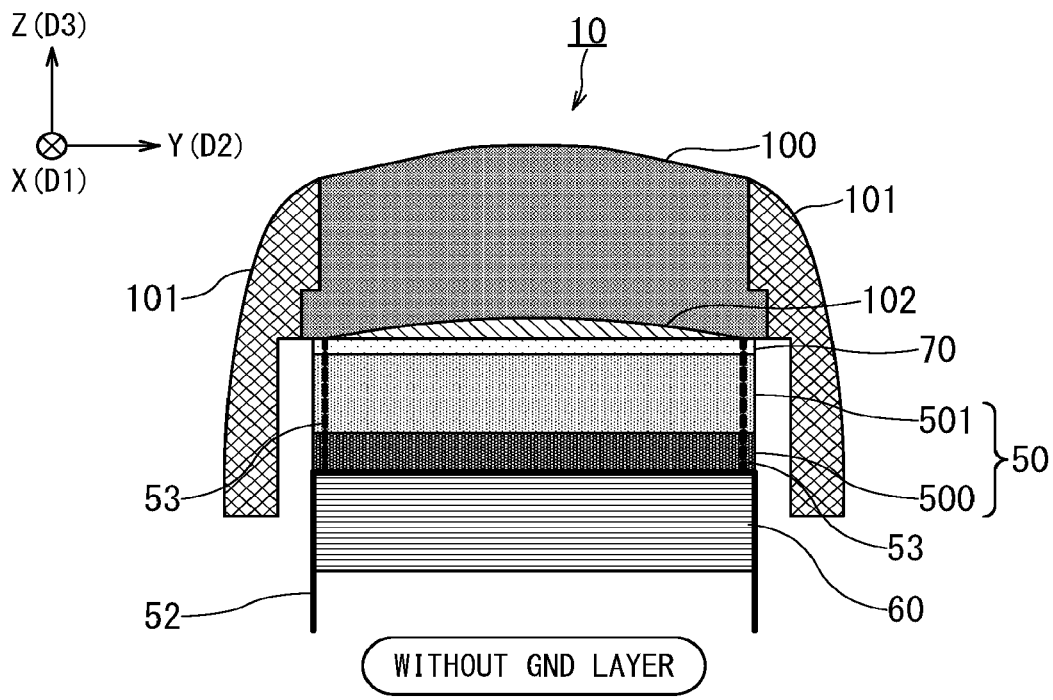
FIG. 5B illustrates the second variation of the probe shown in FIG. 1.

The second variation shown in FIG. 5B configures the probe 10 without the GND layer 51. In this variation, a slit or insulating layer is inserted into the transducer group 50 in the second direction D2 to secure the ground function at the element end. In the second variation, the effective width of the transducer group 50, which is the acoustic effective aperture, is not the width between the ends of the elements but the width between the slits or insulating layers provided near each end of the elements. The slit or insulating layer may be formed on only one end in the second direction D2.

Figure 6:
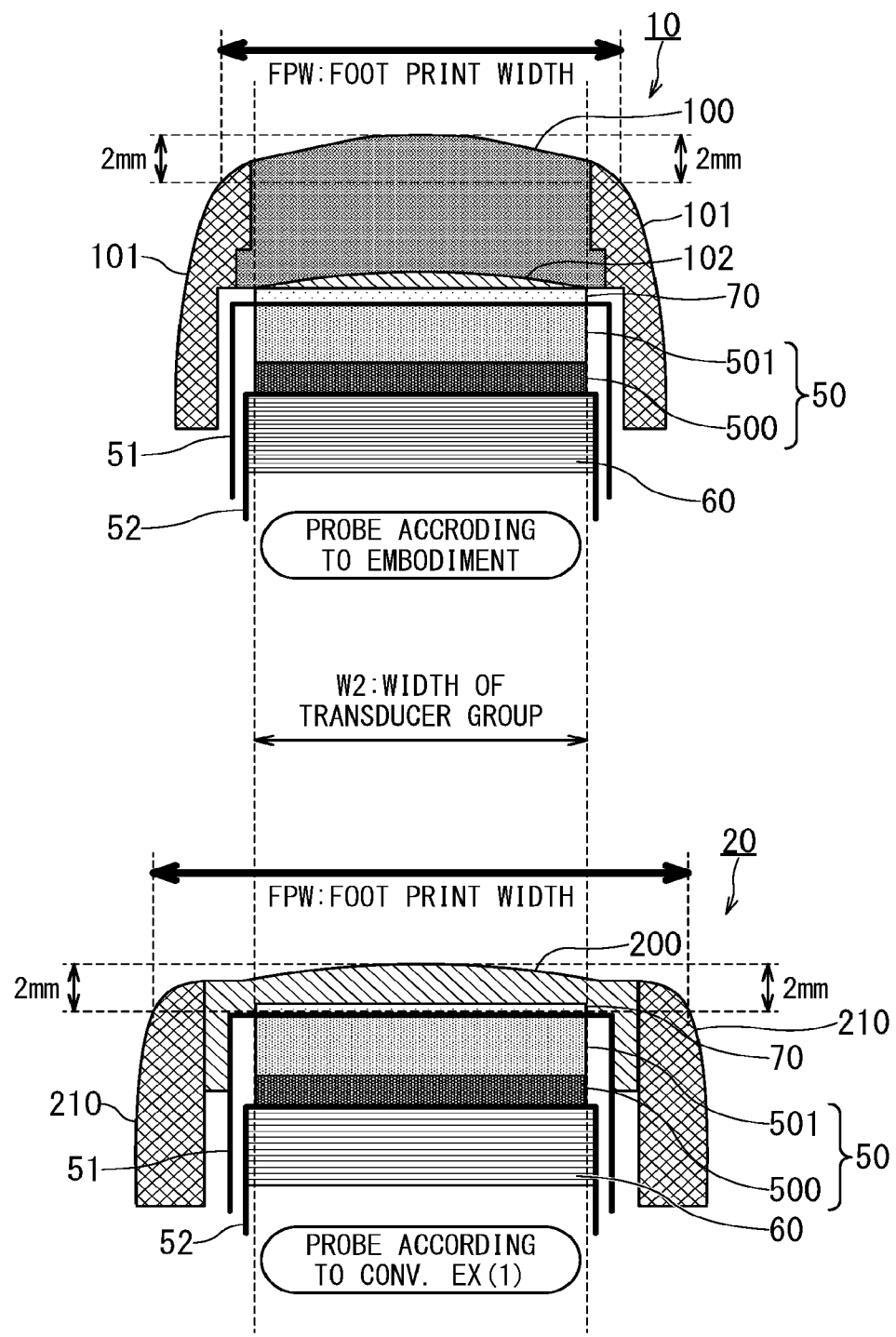
FIG. 6 illustrates a comparison of the foot print widths of the probe shown in FIG. 1 and the probe according to the conventional example (1).

FIG. 6 illustrates a comparison between the foot print widths of the probe 10 shown in FIG. 1 and that of the probe 20 according to the conventional example (1). As mentioned above, the foot print width FPW is defined herein as the width in the second direction D2 at a position 2 mm away from the top of the body contact surface in the lens direction D2.

In FIG. 6, for the probe 10 shown in FIG. 1 and the probe 20 in the conventional example (1), the same definition regarding the footprint width FPW is applied and the same width W2 (acoustic effective aperture) of the transducer group 50 in the second direction D2 is used for comparing the footprint width FPW of the probes 10 and 20.

It is clear from FIG. 6 that the foot print width FPW of probe 10 is smaller than the foot print width FPW of the probe 20 according to the conventional example (1). The reason why the probe 10 can have a smaller foot print width FPW than the probe 20 according to the conventional example (1) has been described above.

Figure 7A:
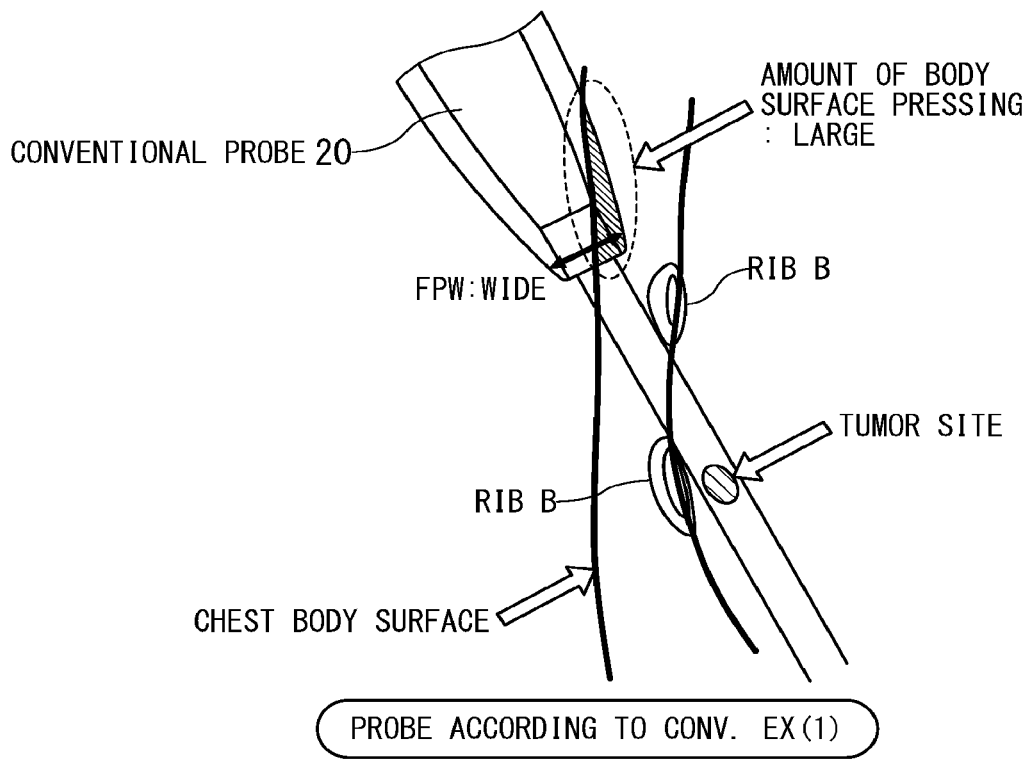
FIG. 7A illustrates problems related to the foot print width FPW of the probe according to the conventional example (1) for comparison with FIG. 7B.

FIG. 7 shows an example of the effect available from the smaller foot print width FPW. FIG. 7A is the same figure as FIG. 3. As shown in FIG. 7A, for example, when trying to check a site such as a tumor behind the rib B, if the body contact width (foot print width FPW) is large, it is necessary to press the probe 20 hard against the body surface that increases the amount of pressure. However, such manipulation of the probe 20 causes pain and discomfort to the patient and places a burden on the patient.

Figure 7B:
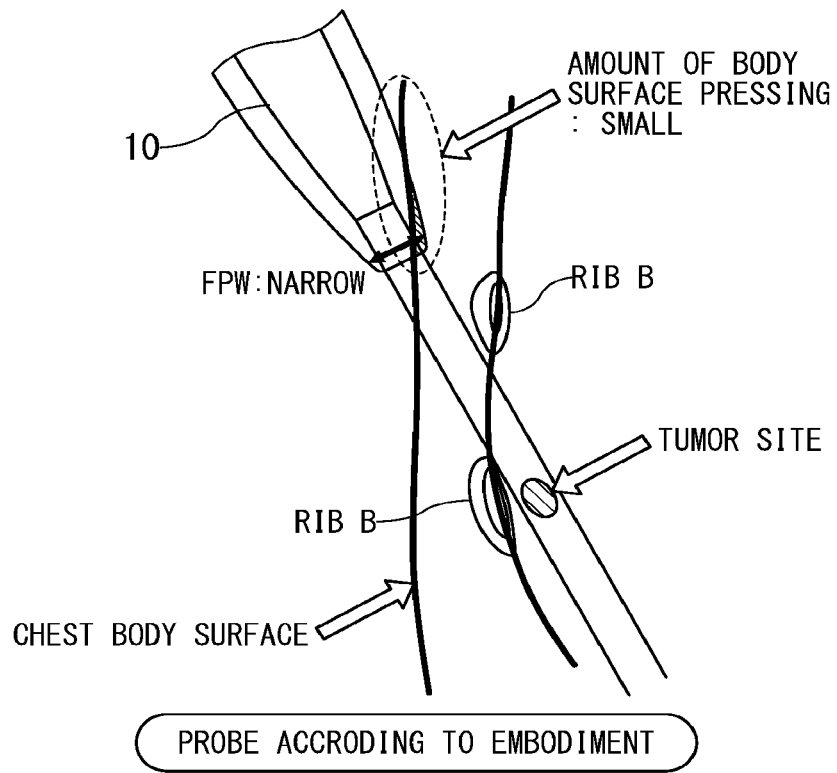
FIG. 7B illustrates an example of the effect of a smaller footprint width.

In contrast, as shown in FIG. 7B, the probe 10 having a small body contact width (foot print width FPW) can reduce the amount of pressure from the probe 10 on the body surface, even when checking a site such as a tumor from the same angle as shown in FIG. 7A. Therefore, according to the probe 10, there is less pain, discomfort, or burden to the patient.

Figure 8:
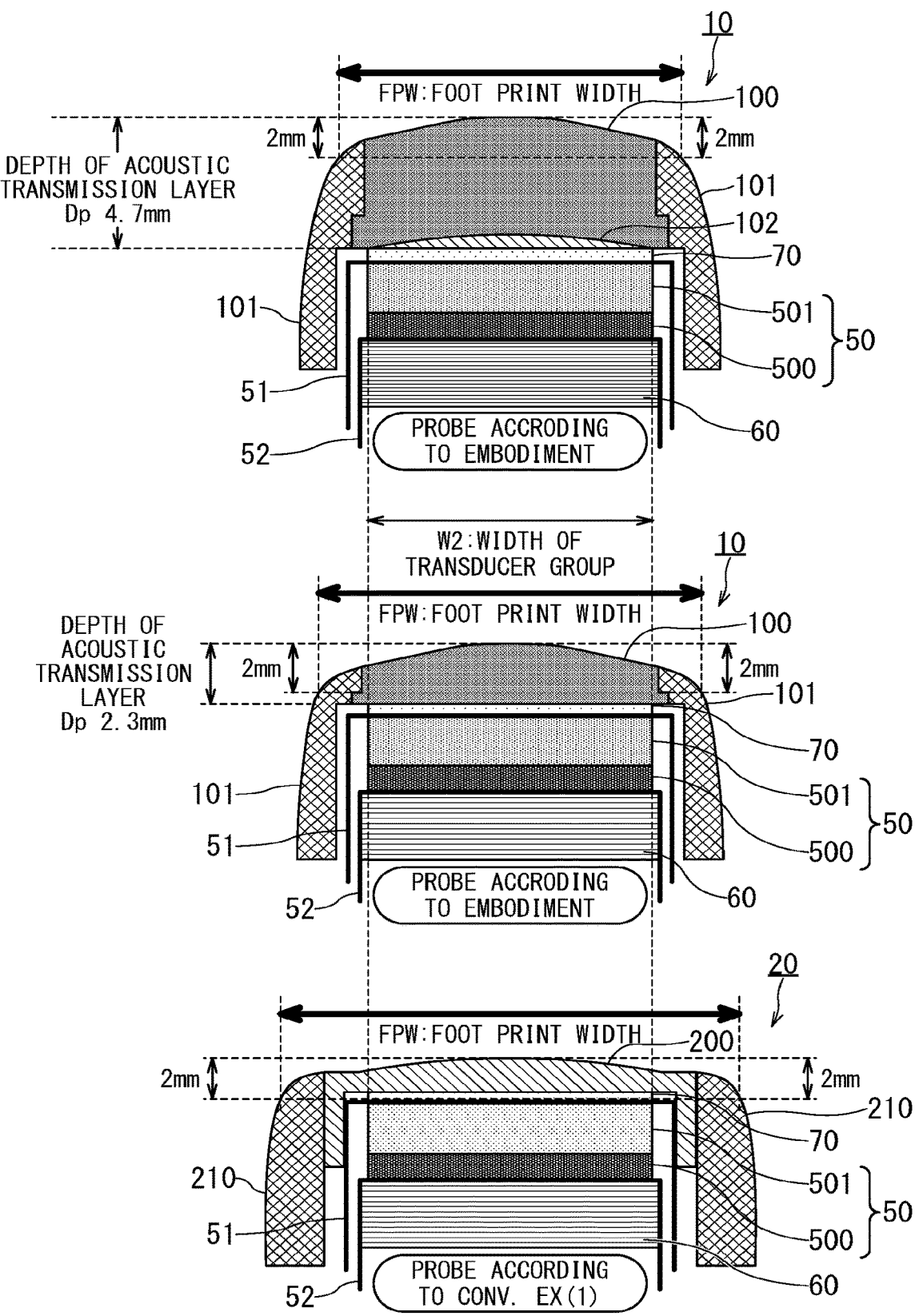
FIG. 8 illustrates the relationship between the footprint width FPW and the distance from the top of the probe surface to the top surface of the transducer group.
Figure 9:
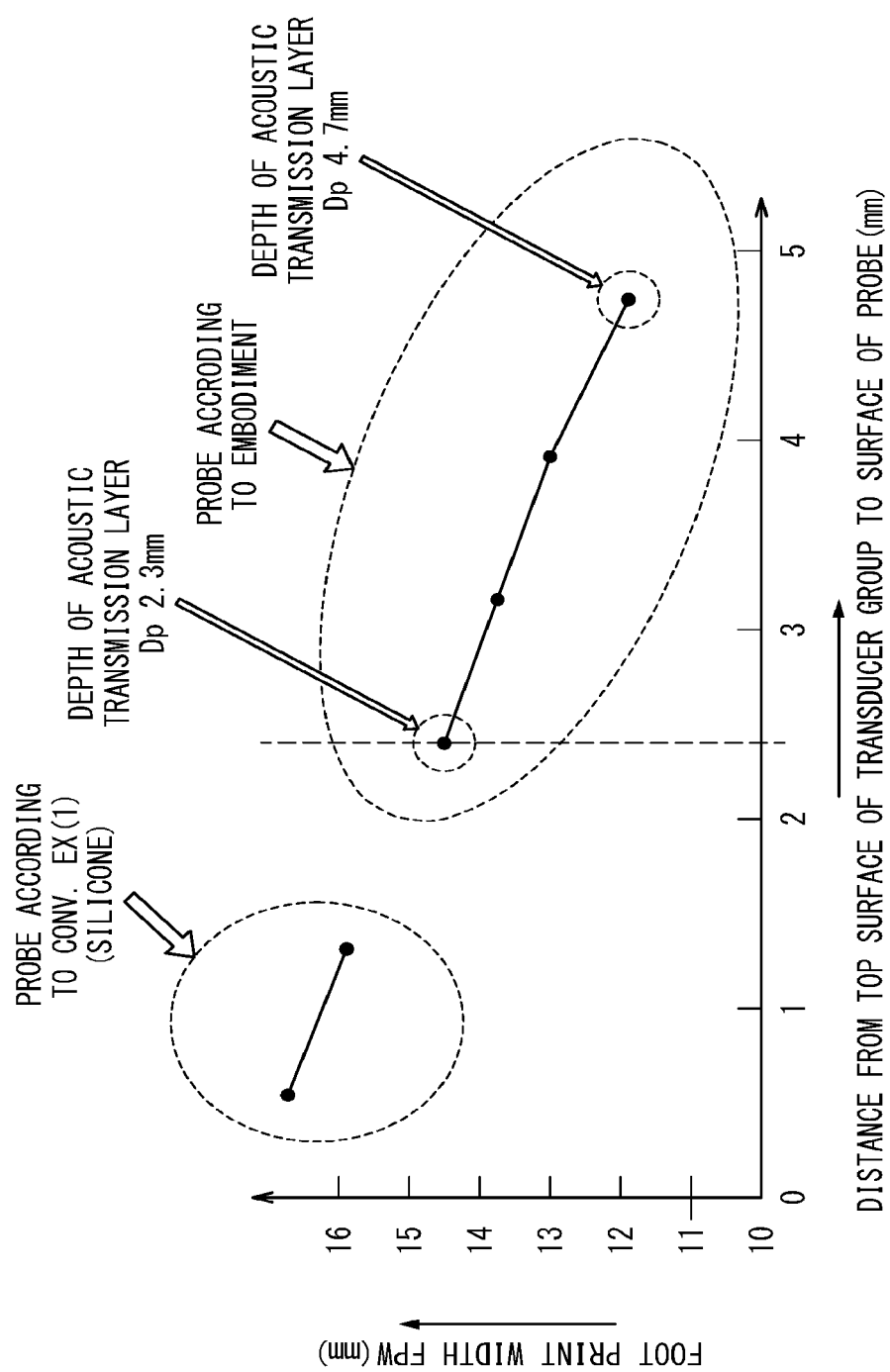
FIG. 9 is a graph illustrating the relationship between the footprint width FPW and the distance from the top of the probe surface to the top surface of the transducer group.

FIGS. 8 and 9 illustrate the relationship between the foot print width FPW and the distance from the top of the probe surface (i.e., the top of the body contact surface of the probe) to the top surface of the transducer group 50 (i.e., the surface between the acoustic transmission layer 100 or the acoustic lens 102 and the transducer group 50 in the probe 10, or the surface between the acoustic lens 200 and the transducer group 50 in the probe 20).

In the structure of the probe 10, it is necessary to secure some adhesion area between the acoustic transmission layer 100 and the cover 101 to maintain reliability. It is also necessary to secure a certain amount of resin thickness of the cover 101 to maintain reliability.

As shown in FIGS. 8A and 8B, in comparison with the case where depth Dp of the acoustic transmission payer 100 is deeper, as the depth Dp of the acoustic transmission layer 100 becomes shallower, the foot print width FPW becomes slightly larger because the radius of curvature R of the body contact surface becomes larger which results in a nearly flat body contact surface.

Taking these factors into account, FIG. 9 shows a graph where the relationship between the distance from the top of the probe surface to the top surface of the transducer group 50 and the foot print width FPW is plotted, when the acoustic effective aperture is fixed at 10 mm and is within the range where manufacture is feasible.

As shown in FIG. 9, when the width in the elevation direction D2 of the body contact surface of the acoustic transmission layer 100 of the probe 10 according to the present embodiment, i.e., the foot print width FPW of the probe 10, is 15 mm or less, then the predetermined distance between the body contact surface of the acoustic transmission layer 100 and the transducer group 50 is 2.3 mm or more.

In FIG. 9, the probe 10 having a distance of about 2.3 mm from the top of the probe surface to the top surface of the transducer group 50 is the probe that minimizes the resin thickness of the cover 101 and the thickness of the acoustic transmission layer 100 (depth Dp of the acoustic transmission layer 100) and corresponds to the probe 10 in FIG. 8B.

In FIG. 9, under the manufacturing constraints of the probe 10, the probe 10 having a distance of about 4.7 mm from the top of the probe surface to the top surface of the transducer group 50 is the probe that maximizes the thickness of the acoustic transmission layer 100 (depth Dp of the acoustic transmission layer 100), thereby maximizing the effect of the invention, which is to minimize the foot print width FPW, and corresponds to probe 10 shown in FIG. 8A.

FIG. 9 also shows the graph where the relationship between the distance from the top of the probe surface to the top surface of the transducer group 50 and the foot print width FPW of the probe 20 according to the conventional example (1) is plotted. As can be seen in FIG. 9, the foot print width FPW of the probe 10 can be smaller than that of the probe 20 according to the conventional example (1) if the distance from the top of the probe surface to the top surface of the transducer group 50 is within the range between about 2.3 mm and about 4.7 mm.

According to at least one of the above-described embodiments, in an ultrasonic probe used in an ultrasonic diagnostic apparatus, the width of the body contact surface in the second direction D2 is reduced, whereby the blind spots in diagnosis through the intercostal space are reduced, and the burden on the patient caused by pressing the ultrasonic probe against the patient can be reduced.

In the above embodiment, the ultrasonic probe 10 is separate from the ultrasonic diagnostic apparatus 41, but the ultrasonic probe 10 may be provided as a part of the ultrasonic diagnostic apparatus 41.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic probe, comprising:
a transducer group having a plurality of transducers transmitting ultrasonic waves;
an acoustic transmission layer transmitting the ultrasonic waves transmitted by the transducer group; and
a protective material protecting the transducer group and the acoustic transmission layer,
wherein a width of the transducer group in an elevation direction and an opening width of the protective material at a position corresponding to the body contact surface of the acoustic transmission layer are substantially identical,
the transducer group is provided at a predetermined distance from the body contact surface of the acoustic transmission layer,
the plurality of transducers of the transducer group is arranged along an azimuth direction,
the protective material covers at least a portion of a lateral side of the transducer group,
in a cross section bisecting a width of the transducer group in the azimuth direction, a distance between an acoustic emitting surface of the transducer group and a top of the body contact surface of the acoustic transmission layer ranges from 2.3 mm to 4.7 mm, and
the acoustic transmission layer is formed using a material with an acoustic impedance between 1.4 MRayl and 1.6 MRayl.

2. The ultrasonic probe according to claim 1, wherein:
the acoustic transmission layer has a convex surface in the elevation direction orthogonal to the azimuth direction; and
the protective material covers at least the portion of the lateral side of the transducer group.

3. The ultrasonic probe according to claim 1, wherein a difference between the opening width of the protective material at the position corresponding to the body contact surface of the acoustic transmission layer and the width of the transducer group in the elevation direction ranges from 0.0 mm to 1.0 mm.

4. The ultrasonic probe according to claim 1, wherein, in the cross section bisecting the width of the transducer group in the azimuth direction, the width of the transducer group in the elevation direction is smaller than an opening width of the protective material in a direction orthogonal to each of the azimuth direction and the elevation direction, the difference between the width of the transducer group and the opening width of the protective material in the elevation direction ranges from 0.0 mm to 1.0 mm.

5. The ultrasonic probe according to claim 1, further comprising an acoustic lens layer that is provided between the transducer group and the acoustic transmission layer and has a sound velocity different from that a sound velocity of the acoustic transmission layer,
wherein the acoustic lens layer has a thickness ranging from 0.3 mm to 0.9 mm and is formed to have a concave surface or a convex surface in a cross section of the elevation direction on a side of the acoustic transmission layer.

6. The ultrasonic probe according to claim 1, wherein the width of the transducer group in the elevation direction is between 6.0 mm and 20 mm, inclusive.

7. The ultrasonic probe according to claim 1, wherein the acoustic transmission layer has a sound velocity between 1500 m/sec and 1600 m/sec, inclusive, and has an attenuation of 0.003 dB/mm/MHz.

8. The ultrasonic probe according to claim 1, wherein the acoustic transmission layer is made from a butadiene rubber-based material.

9. The ultrasonic probe according to claim 1, wherein a convex surface of the body contact surface of the acoustic transmission layer in the elevation direction has an inflection point within the width of the transducer group in the elevation direction.

10. The ultrasonic probe according to claim 1, wherein, when a width of the body contact surface of the acoustic transmission layer in the elevation direction ranges from 0 mm to 15 mm, the predetermined distance between the body contact surface of the acoustic transmission layer and the transducer group ranges from 2.3 mm to 4.7 mm.

11. An ultrasonic diagnostic apparatus, comprising:
the ultrasonic probe according to claim 1.

* * * * *